United States Patent [19]

Jain et al.

[11] Patent Number: 5,396,897
[45] Date of Patent: Mar. 14, 1995

[54] METHOD FOR LOCATING TUMORS PRIOR TO NEEDLE BIOPSY

[75] Inventors: Rakesh K. Jain, Boston, Mass.; Adam Stacy-Clear, Kingston Up Thames, England; Yves Boucher, Belmont, Mass.; Richard Moore, Concord, Mass.; Daniel B. Kopans, Waban, Mass.

[73] Assignee: The General Hospital Corporation, Boston, Mass.

[21] Appl. No.: 58,682

[22] Filed: May 3, 1993

Related U.S. Application Data

[63] Continuation of Ser. No. 821,709, Jan. 16, 1992, abandoned.

[51] Int. Cl.$^6$ ............................................. A61B 5/00
[52] U.S. Cl. ..................................... 128/748; 128/749
[58] Field of Search ............... 128/748, 749, 751, 754, 128/736, 630, 635, 774, 898

[56] References Cited

U.S. PATENT DOCUMENTS

| | | | |
|---|---|---|---|
| 4,162,673 | 7/1979 | Patel | 128/748 |
| 4,192,319 | 3/1980 | Hargens et al. | 128/748 |
| 4,565,200 | 1/1986 | Cosman | 128/642 |

(List continued on next page.)

FOREIGN PATENT DOCUMENTS

| | | | |
|---|---|---|---|
| 59328 | 9/1982 | European Pat. Off. | 128/736 |
| 3900561 | 7/1990 | Germany | 128/748 |
| 2108675 | 5/1983 | United Kingdom | 128/748 |
| 9108702 | 6/1991 | WIPO | 128/748 |

OTHER PUBLICATIONS

Thompson et al "Tumor detection using . . ." 1979 IEEE International Microwave Symposium Digest, pp. 39–44.

(List continued on next page.)

*Primary Examiner*—Stephen C. Pellegrino
*Assistant Examiner*—Guy V. Tucker
*Attorney, Agent, or Firm*—Choate, Hall & Stewart

[57] ABSTRACT

A method for locating a lesion within a tissue mass, includes steps of measuring a selected parameter at two or more points in at least one path through the tissue mass, the measure of the selected parameter in a lesion being different from that in normal tissue. Also, apparatus for measuring a tissue parameter at two or more points in at least one path through the tissue mass includes an insertion needle, distally sharpened and made sufficiently rigid so that it can be inserted distal end foremost into the tissue mass along the path, and, insertible with the needle, a sensor capable of prodding a measure of the tissue parameter at a point in the tissue mass along the path. Where the parameter is selected as one that has a measure different in a lesion type, the apparatus can be used in carrying out the method, whereby a measure at a point in the tissue mass of the selected tissue parameter provided by the sensor indicates that the point is within a lesion. In an embodiment for measuring interstitial fluid pressure in the tissue mass, the sensor includes a tube slidably engageable within the lumen of the insertion needle; the sensor tube is closed at a distal end, and the walls of the sensor tube and the insertion needle are prodded distally with ports, positioned in relation to the respective distal ends such that when the sensor tube is engaged within the insertion tube lumen the ports can be substantially aligned to provide fluid communication between the lumen of the sensor tube and the tissue adjacent the ports; the sensor tube lumen contains a plurality of filaments, and is operationally connected to a pressure measurement deuce such that the pressure measurement deuce is responsive to fluid pressure within the sensor tube lumen.

5 Claims, 1 Drawing Sheet

U.S. PATENT DOCUMENTS

| | | |
|---|---|---|
| 4,616,656 | 10/1986 | Nicholson et al. ............... 128/630 |
| 4,682,605 | 7/1987 | Hoffman ............................ 128/736 |
| 4,790,329 | 12/1988 | Simon ................................ 128/749 |
| 4,799,494 | 1/1989 | Wang . |
| 4,799,495 | 1/1989 | Hawkins et al. . |
| 4,940,458 | 7/1990 | Cohn ..................................... 604/51 |
| 4,986,279 | 1/1991 | O'Neill . |
| 5,018,530 | 5/1991 | Rank et al. ........................ 128/749 |
| 5,059,197 | 10/1991 | Urie et al. .......................... 606/116 |
| 5,078,137 | 1/1992 | Edell et al. ........................ 128/635 |
| 5,222,953 | 6/1993 | Dowaltshahi ...................... 606/15 |

OTHER PUBLICATIONS

Fadnes, et al., "Interstitial Fluid Pressure in Rats Measured With a Modified Wick Technique" 1977, *Microvascular Res.*, vol. 14, pp. 27–36.

Boucher, et al., "Interstitial Pressure Gradients in Tissue-Isolated and Subcutaneous Tumors: Implications for Therapy", Aug. 1, 1990, *Cancer Res.*, vol. 50, pp. 4478–4484.

Young, et al., "The Significance of the Tissue Pressure of Normal Testicular and of Neoplastic (Brown–Pearce Carcinoma) Tissue in the Rabbit", 1950, *J. Path. Bact.*, vol. LXII, pp. 313–333.

Boucher, et al., "Interstitial Hypertension in Superficial Metastatic Melanomas in Humans", Nov. 8, 1991, *Cancer Res.*, vol. 51, pp. 6691–6694.

Roh, et al., "Interstitial Hypertension in Carcinoma of Uterine Cervix in Patients: Possible Correlation With Tumor Oxygenation and Radiation Response", Nov. 8, 1991, *Cancer Res.*, vol. 51, pp. 6695–6698.

Kopans, et al., "A Modified Needle-Hookwire Technique to Simplify Preoperative Localization of Occult Breast Lesions", 1980, *Radiology*, vol. 134, p. 781.

Meyer, et al., "Preoperative Roentgenographically Guided Percutaneous Localization of Occult Breast Lesions", Jan. 1982, *Arch. Surg.*, vol. 117, pp. 65–68.

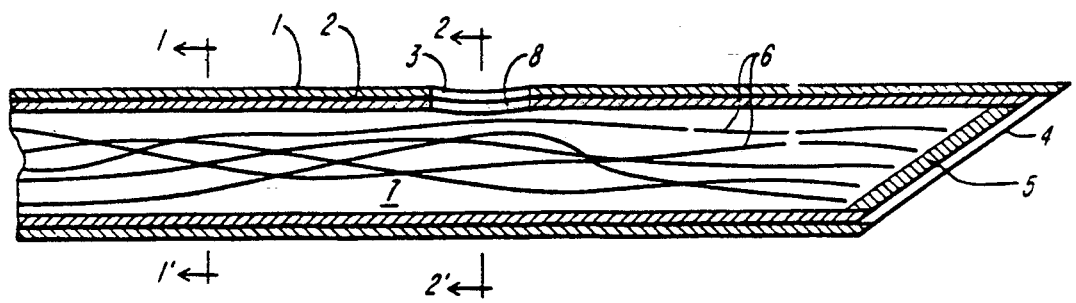
FIG. IA
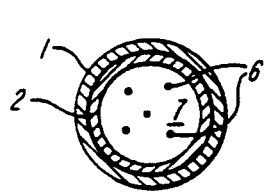
FIG. IB
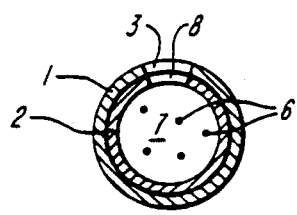
FIG. IC
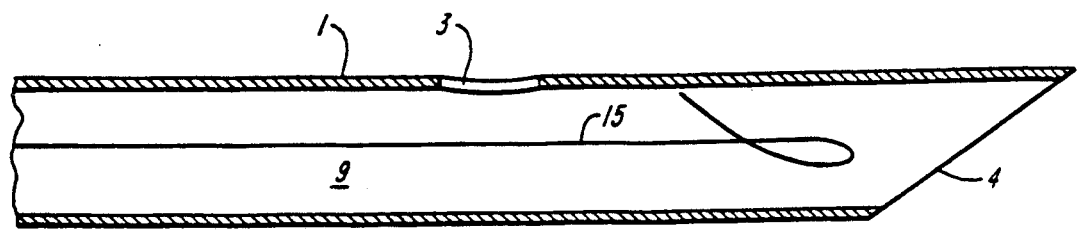
FIG. ID

METHOD FOR LOCATING TUMORS PRIOR TO NEEDLE BIOPSY

BACKGROUND OF THE INVENTION

This is a continuation of application(s) Ser. No. 07/821,709, filed on Jan. 16, 1992, now abandoned.

This invention was made in the course of work supposed in part by the United States Government, and the Government has certain fights in the invention.

This invention relates to the localization and diagnosis of lesions in vivo. "Lesion" as used herein is a pathologic change in tissue, such as for example a tumor. Lesions that are too small to be found by palpation are conventionally located using imaging techniques and surgically removed. For example, breast lesions can be detected by mammogram as much as four years earlier than by physical examination. However, a mammogram is unable to distinguish a benign from a malignant lesion, and detection of a lesion by mammography must be followed by biopsy. Because a mammogram has a positive predictive value of 20-30%, a large proportion of breast biopsies following mammography prove to be for nonmalignant lesions. A reduction in the number of breast biopsies performed for benign disease would be extremely imposer and beneficial.

In conventional mammogram-assisted screening for breast disease, a mammogram of the breast is made, and the resulting image is inspected for lesions. If a small lesion appears, a radiopaque needle is inserted into the breast in a region as near as can be estimated to the lesion. Then the region is imaged with the needle in place, the resulting image is inspected, and the needle is relocated as necessary to place it witch the lesion. Once the needle appears to be positioned within the lesion, the surgeon follows the needle to the lesion and removes the lesion and surrounding tissue, and the pathological status of the lesion can be determined. Because the imaging procedure provides only an estimate of the proximity of the biopsy needle to the lesion, it may often be necessary, in the interest of removing all the lesion, to remove a substantial quantity of normal surrounding tissue as well.

The positioning of a biopsy needle in soft tissue as a marker for lesions has been found to be unreliable, because the biopsy needle can move during the preparation of the patient for surgery. Kopans et al. (1980, *Radiology*, Vol. 134, p. 781) describe inserting a hookwire into the lesion via the lumen of the hollow needle used during the imaging procedure to localize the lesion. After the hookwire is in place the needle is withdrawn, leaving the hookwire in a position estimated to be closest to the lesion. This needle-hookwire approach has been used successfully to provide a more secure marker for breast biopsies (Meyer et al., 1982, *Arch. Surg.*, Vol. 117, pp. 65-68). However, once the hookwire is implanted in the tissue, it cannot be removed without tissue damage except by surgery.

Since the development of needle-hookwire assembly by Kopans et al., other breast biopsy needles have been developed. For example, biopsy needles have been designed with retractable barbs to anchor the biopsy needle in tissue, and to facilitate the removal of the needle in case of incorrect positioning, or in case it is desirable to remove the localization needle during surgery without requiring surgical removal of excess tissue (U.S. Pat. Nos. 4,986,279; 4,799,495). In each of these biopsy needle localization systems, the proximity of the biopsy needle to a lesion is estimated by imaging techniques.

The effectiveness of therapies currently used for the treatment of lesions, as for example solid tumors, is limited by the capacity of the therapeutic to reach the target in vivo in adequate quantities. In animal studies, solid tumors have been shown to contain a greater volume of interstitial fluid—that is, of fluid in the extracellular and extravascular space, than normal tissues contain, suggesting that tumors should be readily infiltratable by therapeutic macromolecules. However, additional animal studies have demonstrated that the interstitial fluid pressure ("IFP") is higher in tumors than in normal tissues, resulting in poor perfusion of tumors by therapeutic molecules and a radially outward convection of interstitial fluid from tumors (reviewed in Jain, 1987, *Cancer Res.*, Vol. 47, pp. 3039-3051).

An examination of the microvascular network of rat mammary adenocarcinoma tumors was conducted to aid in understanding the distribution of blood flow and its influence on the exchange and uptake of relevant molecules in chemotherapy, immunotherapy, or radiation treatment (Less et al., 1991, *Cancer Res.*, Vol. 51, 265-273). The results of this study indicated that the bifurcation geometry and network structure in tumor vasculature may be one mechanism responsible for the increased resistance to blood flow reported in tumors (Sevick et al., 1989, *Cancer Res.*, Vol. 49, pp. 3506-3512).

The elevated IFP of tumors was first described by Young et al. (1950, *Jour. Pathol. Bacteriol.*, Vol. 62, pp. 313-333) after taking "tissue pressure" measurements in rabbits. Each of three methods for measuring local interstitial pressure, known as the needle method, wick-in-needle method, and micropiper method, has advantages and limitations. In the needle method, a needle filled with physiological saline and coupled to a pressure measuring device is inserted into tissue. In the wick-in-needle method, fibers of polyester or other multifilamentous material are placed within the lumen of the needle in order to provide a large surface area continuum with the interstitium and reduce occlusion. Both of these methods can cause tissue distortion. In the micropipet method a micropiper connected to a servo-null pressure-measuring system is used, reducing some problems presented in the needle and wick-in-needle methods, but the micropipers are susceptible to breakage.

The IFP of subcutaneous tumors was measured in rats using micropipets (Boucher et al., 1990, *Cancer Res.*, Vol. 50, 4478-4484). This study describes a steep IFP gradient that begins at the surface of the tumor, or the skin/tumor interface, and quickly reaches a plateau value in the tumor mass within 0.2-1.1 mm of the tumor surface. These results confirmed an earlier mathematical model of interstitial fluid transport in tumors (Jain et al., 1988, *Cancer Res.*, Vol 48, pp. 7022-7032) which proposed that very little filtration of macromolecules into tumors occurs even from blood vessels which pass through the tumor, and that the convective outward flow of the interstitial fluid pushes solutes toward the periphery. These conclusions are also supported by work from Dvorak et al. (1988, *Am. Jour. Pathol.*, Vol. 133, pp. 95-105) who demonstrated that small molecules can readily penetrate tumors, and large macromolecules are limited to the tissue-tumor interface. The inability of therapeutic drugs to reach the center of tumors has grave implications for cancer therapies, and based upon these results Boucher et al. (1990) proposes methods by which drug delivery to tumors could be enhanced.

The wick-in-needle technique was developed by Fadnes et al. (1977, *Microvasc. Res.*, Vol 14, pp. 27–36). Fadnes et al. describes a thin hypodermic needle open at the end and having a side-hole, its lumen filled with multifilamentous nylon thread and connected by polyethylene tubing to a pressure transducer. Fadnes et al. describes using this pressure-sensing needle to compare the subcutaneous IFP in anesthetized rats under normal and dehydrated conditions.

The interstitial fluid pressure of human melanomas and uterine cervix carcinomas was measured using the wick-in-needle technique in studies that demonstrated for the first time in humans that IFP is higher in tumors than in normal tissue. Boucher et al. (1991), *Cancer Res.*, Vol. 51, pp. 6691–6694, demonstrated that the IFPs of large human melanomas far exceed the values expected from measurements of rodent tumors or human xenografts. Roh et al. (1991), *Cancer Res.*, Vol. 51, pp. 6695–6698, demonstrated that a lowering of the IFP in some cervical tumors during fractionated radiation therapy correlates well with therapeutic outcome. Both Boucher et al. and Roh et al. conclude that the IFP of tumors will be valuable for designing future cancer therapies and predicting treatment outcome.

K. P. Wang, U.S. Pat. No. 4,799,494, describes a needle assembly for collection of lung tissue. The needle assembly includes a blunt hollow outer needle having a side-hole for tissue collection, and a non-removable inner hollow needle attached to a solid wire, slidably engaged within and snugly fitting the lumen of the outer needle, used for piercing the tissue. The lumen of the outer needle is connected to a crude balloon pressure sensor. The '494 patent states that the localization of the needle tip in the lung lesion to be sampled results in a pressure decrease detectable at the balloon.

SUMMARY OF THE INVENTION

We have discovered that a lesion can be accurately located within a tissue mass by measuring, at several points in a path through the tissue mass, a selected parameter that is known to measure differently in lesions (or at least in some types of lesions) and in normal tissues; and we have developed apparatus for carrying out such measurements, particularly of interstitial fluid pressure.

Using the method, the location and, at least to some extent the size and the boundary of a lesion can be determined accurately and without a requirement for repeated reimaging of the tissue mass. Moreover, some selected parameters can, depending upon the extent of deviation of their measure from normal, provide information regarding the pathological condition of the lesion; for example, some parameters deviate more from normal in malignant tumors than in benign lesions.

In one aspect, the invention features a method for locating a lesion within a tissue mass, including measuring a parameter at a plurality of points in at least one path through the tissue mass, the measure of the parameter in lesions being different from the measure in normal tissue.

In preferred embodiments, the parameter is interstitial fluid pressure, and more than one parameter may be measured at one or more of the points; the method may further include a step of inserting a tissue marker, such as a hookwire, into the lesion along a portion of the path, to mark the lesion for subsequent removal.

Typically, the method of the invention may be used to mark the location of, and if desired to gain additional information as to the condition of, a lesion located by imaging or by palpation.

In another general aspect, the invention features apparatus for measuring a tissue parameter at a number of points along at least one path through the tissue mass, including an insertion tube, sharpened at a distal end and made sufficiently rigid so that it can be inserted distal end foremost into the tissue mass along the path, and, insertable with the insertion tube, a sensor capable of providing a measure of the tissue parameter at a point in the tissue mass along the path.

According to the invention, apparatus for locating a lesion in a tissue mass includes such apparatus for measuring a selected tissue parameter at a number of points along one or more paths through the tissue mass; at any point in the tissue mass a measure by the sensor of the selected parameter that is distinguishably different from that in normal tissue indicates that the point is within a lesion.

In preferred embodiments the tissue parameter is interstitial fluid pressure and the sensor includes a pressure sensor. The wall of the insertion tube includes a port near its distal end, and the sensor includes a sensor tube, containing filaments, slidably engageable within the lumen of the insertion tube; the sensor tube is distally closed and has a port near its distal end, and the ports are positioned so that when the sensor tube is engaged within the insertion tube lumen the ports can be substantially aligned to provide fluid communication between the lumen of the sensor tube and the tissue adjacent the ports; and the sensor tube lumen is operationally connected to a pressure measurement device such that it is responsive to fluid pressure within the sensor tube lumen.

The apparatus of the invention makes use of a thin-walled fine-gauge distally sharpened needle for the insertion tube, so that by use of the apparatus the method of the invention can be carried out without anesthesia. The pressure-sensing apparatus according to the invention can be used to accurately determine the interstitial pressure within a lesion in approximately 10 minutes' time. The invention provides for reliable measurements of interstitial fluid pressure in any variety of types of lesions in any of a variety of tissues with a minimum of discomfort to the patient.

The invention can provide for estimating the location, size and biological potential of a lesion by measuring the interstitial fluid pressure, by passing the insertion tube, with the associated sensing device, into tissue that has been shown by palpation or imaging techniques to contain a lesion (such as a tumor), in a path that is estimated to pass through the lesion, and measuring the pressure at multiple points along the path. "Biological potential" as used herein encompasses all pathological types of lesions, including benign lesions.

The higher IFP of a lesion allows the operator, making several measurements along the path, to determine when the insertion needle has both entered and exited the lesion. The IFP of a lesion can additionally be indicative of its biological potential. In malignant lesions the IFP is elevated above the IFP of normal tissue and the IFP increases with lesion size. In benign lesions, on the other hand, the IFP may be comparable to that of normal tissue.

Insertion of the sensor through the lesion along more than one path allows the IFP and the entry and exit points to be determined along more than one transect of the lesion. The size and extent of the lesion and its biological potential can then be estimated. Preferably, the IFP of the lesion is measured in two different locations, and the IFP is recorded first of normal tissue then repeatedly at close intervals or continuously as the needle is advanced into the lesion and exits the lesion into normal tissue again. The pressure reading for the excursion of the insertion needle along each path takes approximately 10 minutes, and the entire procedure takes approximately 20 minutes to complete.

For example, where palpation or mammography has shown that a lesion is present in the breast, the interstitial fluid pressure of the lesion can be determined as described above, and if the interstitial fluid pressure indicates a benign lesion then the patient will not need to undergo surgery. If, on the other hand, the pressure measurement indicates a malignant lesion, a hookwire can be very accurately placed within the lesion as a marker for the subsequent surgical removal.

DESCRIPTION OF THE PREFERRED EMBODIMENTS

Drawings

FIG. 1A is a longitudinal section of part of a pressure-sensing needle assembly, according to the invention, showing the positions of the components.

FIG. 1B is a cross-sectional view thru 1—1' of the pressure-sensing needle assembly of FIG. 1A.

FIG. 1C is a cross-sectional view thru 2—2' of the pressure-sensing needle assembly of FIG. 1A.

FIG. 1D is a longitudinal section of a needle assembly, according to the invention, showing a hookwire within the lumen of the insertion needle.

GENERAL DESCRIPTION

In the method according to the invention, the location of a lesion within a tissue mass is accurately determined by measuring a parameter, known to measure higher or lower within such lesions than in normal tissues, at a plurality of points in one or more paths through the tissue mass. Any one or more of a variety of parameters can be measured according to the invention; in particular, elevated interstitial fluid pressure within a lesion can be a reliable indicator not only of the location and size of the lesion, but also of its biological potential; for example, malignant tumors can have interstitial fluid pressures elevated to a greater degree than benign tumors. Moreover, apparatus for introducing the sensor into the tissue mass can be provided with two or more sensors, capable of detecting more than one parameter. Some such parameters can be selected to aid in locating the lesion or in diagnosing its pathological condition, and others can provide information that may be useful to medical personnel who subsequently treat the lesion.

An accurate sensor for carrying out the method of the invention can conveniently be associated with a fine-gauge, thin-walled tube, made sufficiently rigid and sharpened so that it can be passed into the tissue mass without causing intolerable discomfort to the subject; a sharpened hollow needle such as a fine-gauge biopsy needle may be suitable, for example. Where initial imaging methods indicate the presence of a lesion within a tissue mass, the hollow sharpened needle with the associated sensor is inserted into the tissue mass along a direction estimated to pass into the lesion, and measurements are made at close intervals. If the measurements do not indicate that the sensor has passed into a lesion, the needle and sensor can be withdrawn and reinserted along a different path. These steps can be repeated until the lesion has been located and sufficient information has been obtained to provide an indication for biopsy; repeated reimaging is unnecessary. Once the sensor indicates that the needle has passed into a lesion, it can be passed further into the tissue mass and further measurements can be made along the path, until the measurements indicate that the sensor has passed through and out from the lesion into normal tissue. A record of the positions along the path where the measurements were made can provide an estimate of the dimension of the lesion along the line of the path. Then the needle can be partly withdrawn, so that its open tip is again within the lesion. Then a marker, such as for example a hookwire, can be introduced via the needle to a point within the lesion near the needle tip, and the needle can be withdrawn, leaving the marker in place.

By way of example, an embodiment of apparatus for lesion localization and diagnosis according to the invention is described below, including a pressure sensor insertable into a thin-walled hollow insertion needle. The pressure sensor itself includes a hollow tube containing filaments, dimensioned and configured so that it slides within the lumen of the hollow insertion needle in sealed relation to the needle wall. The filament-containing sensor tube is closed at its distal end; and the walls of the sensor tube and of the insertion needle are each provided with a port near the distal end, and the ports are alignable to provide communication between the interstitial fluid surrounding the insertion needle and fluid within the lumen of the sensor tube. A pressure measuring device is operatively connected to the sensor tube so that it is responsive to the hydrostatic pressure within the sensor tube lumen, providing a measure of the interstitial fluid pressure in the tissue mass near the insertion needle adjacent the ports.

APPARATUS

The distal portion of an embodiment of apparatus for lesion localization and diagnosis according to the invention, including a pressure sensor insertable into a thin-walled hollow insertion needle, is shown by way of example in a diagram in FIG. 1A and in sectional views in FIGS. 1B and 1C.

With reference now to FIG. 1A, the pressure-sensing apparatus, a distal portion of which is shown, includes a fine-gauge, thin-walled hollow insertion needle 1 and, shown in operative relation within insertion needle 1, a removable hollow inner sensor tube 2. Within the lumen 7 throughout the length of sensor tube 2 are filaments 6. Sensor tube 2 is operatively connected to a pressure measurement device (not shown in the Figs.) in such a manner that the pressure measurement device is responsive to hydrostatic fluid pressure within the lumen 7 of sensor tube 2. The distal tip 5 of sensor tube 2 is plugged, while the insertion needle 1 is left open. A port 3 in the wall of the insertion needle 1 and a port 8 in the wall of sensor tube 2 are substantially aligned when the insertion needle and sensor tube are in operational relation, as shown in the Figs.

In one embodiment, the insertion needle 1 is a 20 gauge stainless steel needle, and port 3 is a 2-3 mm hole, located 2 cm from the open sharp distal insertion needle tip 4. Sensor tube 2 is a stainless steel hollow needle, 23 gauge so that it fits snugly within insertion needle 1, and port 8 is a 2–3 mm hole, located about 2 cm from the distal sensor tube tip 5, which is sealed with solder. The sensor tube 2 contains within its lumen 7 and throughout its length 4–5 monofilamentous surgical suture fibers 6, preferably 6-0 ethilon or other monofilamentous nylon of the same size, which occupy the length of the inner needle 2.

Insertion needle 1 and sensor tube 2 are each provided at the proximal end (not shown in the Figs.) with a plastic hub for ease in manipulation by the user, as is well-known in the needle biopsy art. Alignment marks on the plastic hubs (not shown) are provided to aid the user infolding the ports 3, 8 in alignment during use, as shown in FIGS. 1A, 1C. When the ports 3, 8 are aligned substantially as shown in the Figs., they provide for direct communication between fluid in the sensor tube lumen 7 and the interstitial fluid in tissues outside the insertion needle 1 near the ports.

Sensor tube 2 is operatively connected to a pressure measurement device (not shown in the Figs.), such as the model P23XL pressure transducer available from Spectramed Inc., Oxnard, Calif., by way of noncompliant sterilized plastic tubing filled with sterile heparinized saline, preferably 70 Units/ml, connected between the pressure transducer and the proximal end of the sensor tube. The pressure transducer is connected to signal processing means, such as, for example a preamplifier, and a recorder or other data storage device. In one embodiment the signal from the transducer is sent through a preamplifier, such as the model 11-4113-01 available from Gould Inc., Cleveland, Ohio, and the amplified signal is sent to a dual-channel chart recorder, such as the model 30-V7202-11 available from Gould Inc.; or the amplified signal is digitized and stored.

The lengths of the sensor tube 2 and insertion needle 1 are selected to be sufficiently long to reach to the expected path length within the tissue mass to the deepest measurement point. The lesion is located and the tip of the insertion needle is relocated within the lesion as described above, General Description, and the sensor tube is withdrawn from the insertion needle. Then, as shown in FIG. 1D, a flexible hookwire 15 such as, for example, a 0.03 cm diameter hookwire having 22,600 kg/cm$^2$ tensile strength, 11.4 kg breakload or, for example, a 0.02 cm diameter hookwire having 20,000 kg/cm$^2$ tensile strength, 6.5 kg breakload, is inserted into the tissue by way of the lumen 9 of the properly emplaced insertion needle. Then insertion needle 1 is withdrawn from the site, leaving the hookwire 15 implanted in the lesion as an accurate marker of the position of the lesion. The portion of the hookwire that emerges from the wound (not shown) is taped to the subject's skin until surgery. If desired, the outer needle 1 can be reintroduced over the hookwire during surgery to provide a firm guide for the surgeon's knife.

The embodiment described above with respect to the Figs. is particularly adapted for use in localizing breast lesions. As will be appreciated the dimensions of the insertion tube can differ from those described, and for some given applications, e.g. investigations of lesions in other tissue masses or in children, the diameter may preferably be larger or smaller. Needles as large as 16 or 18 gauge may be used depending upon the tissue to be pierced, and smaller gauge needles may be used so long as they are sufficiently rigid to permit insertion into the tissue mass. The diameter of the sensor tube will be chosen accordingly to provide a snug fit within the insertion tube. The material of the insertion tube need not be stainless steel yet must be chosen to provide sufficient rigidity for insertion into the tissue containing a lesion. The material of the sensor tube need not be stainless steel. The sensor tube also does not need to be as rigid as the insertion tube, as it is carried within and supported by the insertion tube. The filaments contained within the sensor tube can be any type of nonabsorbent monofilament, and the size of each filament and the number of filaments placed within the sensor tube can be easily determined without undue experimentation. The filaments function to aid the fluid communication between the sensor and the tissue without occluding the lumen of the sensor, and for example the placement of 6 or 7 filaments, of the type described above, within the lumen of a 23 gauge sensor may too completely fill the lumen of the sensor and cause too much resistance. The port of the insertion tube and the sensor tube can be located at varying distances from the distal end, as is convenient. Positioning the ports as little as 4–5 mm from the distal end of the insertion needle can yield less satisfactory results; and, if the ports are located much further than 2 cm behind the tip then the tip may be situated inconveniently far beyond the lesion when the port is located within it. The distal end of the sensor tube is preferably closed in order to restrict the measurement of the parameter to a single region of the lesion or tissue, and to prevent incursion of tissue into the end as the insertion tube is passed into the tissue mass.

USE

The pressure measuring apparatus according to the invention can be used for measuring the interstitial fluid pressure in tissues, and for locating lesions in the tissues, at any of various sites within the subject's body.

Preferably the apparatus is calibrated just prior to use. Such calibration can conveniently be performed using a water column, and a zero reference point is preferably obtained by placing the sensor tube tip and insertion needle tip at skin level. The user then introduces the insertion needle, containing the sensor tube in proper alignment as indicated by the alignment marks on the hubs, into the tissue mass at a point where the ports can be expected to be situated in normal tissue. Then proper communication between the saline in the lumen of the sensor tube and the interstitial fluid in the tissues can be checked as follows. First the plastic tubing connecting the pressure transducer with the sensor tube is compressed with a screw clamp. This displaces a small amount of fluid within the tubing and the lumen of the sensor tube, which should cause a transient rise in the pressure measured by the transducer; the fluid should, provided that there is proper fluid communication, quickly thereafter pass from the sensor tube through the ports into the surrounding tissues, allowing the pressure measurement to return quickly to normal. The clamp is then released, decompressing the tubing and causing a transient decrease in the pressure at the transducer, which should again quickly return to normal. The pressure sensing tube lumen may be considered to have proper fluid communication with the interstitial fluid of the tissues if, following compression and decompression in such a test, the stable value measurements are within 15% of each other.

The apparatus is then advanced into the tissue and the interstitial fluid pressure is continuously recorded (or recorded at closely-spaced intervals). As the apparatus enters a lesion, and the interface between normal tissue and a malignant lesion interface is pierced, the passage through the interface of the ports is expected to be observed as a sharp and marked increase in pressure. The depth of the needle at the interface is recorded, and then the needle is advanced further into the tissue through the lesion. As the apparatus reaches the distal lesion/normal tissue interface, the passage through the interface by the ports as they leave the lesion mass is observed at the lesion/normal tissue interface as a sharp and marked decrease in the measured interstitial fluid pressure, the pressure rapidly falling from the internal pressure of the lesion to the expected pressure of normal tissue. Using this method a series of measurements along a path requires approximately 10 minutes to complete.

Proper fluid communication between the needle and the interstitial fluid of the lesion can be confirmed by compressing and decompressing the tubing while the needle is stationary within the lesion. One may wish to complete this additional step when the measured IFP within a lesion is very low or comparable to the pressure in normal tissues, in order to ensure the accuracy of the measurement, particularly as a low IFP within a lesion can be indicative that the lesion is benign.

The procedure outlined above can then be repeated using another pressure sensing assembly at a different location within the lesion. Two independent measurements of the IFP within a lesion can improve the accuracy of the diagnosis, and determination of the entry and exit points of the needle along two (or more) paths within a lesion will allow a more accurate estimation of the size of the lesion.

Once the location of the lesion has been accurately determined the sensor tube is withdrawn from the insertion needle, leaving the insertion needle in situ, and a hookwire is inserted via the insertion needle lumen into the tissue at the insertion needle tip. The insertion needle is then withdrawn from the tissue mass, leaving the hookwire implanted in the lesion as an accurate and secure marker of the location of the lesion.

OTHER EMBODIMENTS

Other embodiments are within the following claims.

For example, measuring devices other than the fiber-containing tube described above could be could be used in association with the insertion needle to measure the interstitial pressure. Available pressure measuring devices that can be adapted for use in the invention include devices based upon the piezoelectric effect or upon flexion of fiber optic devices. Such alternate pressure measuring devices may have the benefit of significantly reducing the length of time required to accurately determine the interstitial fluid pressure.

Measurements of indicia other than IFP which show the presence of a lesion at a given point in tissue, and therefore of the location of the lesion within the tissue mass, can be used in place of or in addition to IFP measurements. Other parameters which can be measured include, for example, interstitial fluid pH or oxygen tension ("$pO_2$"). Preliminary results indicate that the extracellular pH of a malignant lesion can be lower than that of normal tissue, and that the $pO_2$ of a malignant lesion can be lower than that of normal tissue. Measurements of such parameters, preferably simultaneously with and at the same measurement points as the pressure measurements, can corroborate the diagnosis provided by the pressure measurements. Moreover, the choice of therapeutic method for treating a lesion can be substantially benefitted by measuring certain tissue parameters within the lesion other than pressure. Some therapeutic compositions are known to be more or less effective than others at the particular pH or at the $pO_2$ encountered within a given lesion. For instance, a lesion having a low interstitial pH could immediately be treated with drugs which are known to be more effective in acidic environments. Thus the knowledge of the environment within a lesion will provide the clinician with information which allows decisive and effective implementation of drug or radiation therapies.

The assembly according to the invention, as described generally and particularly above, can readily make use of a sensor device, capable of measuring one or more parameters other than pressure, adapted for introduction by way of an association with (as, for example, within the lumen) an insertion needle. For instance, once the lesion has been located as described above, the pressure sensor tube can be withdrawn and a fiberoptic sensor put in its place, capable of measuring pH, $pO_2$, $pCO_2$, and the temperature within the lesion. A fiber optic sensing device capable of taking such measurements and adaptable for use according to the invention has been developed, for example, by Puritan-Bennet Corp., (see, e.g., *IEEE Spectrum*, 1992, Vol. 29, pp. 61 et seq.).

We claim:

1. A method for determining the locus of a pathologic condition within a tissue mass, comprising the steps of:
   (a) inserting into the tissue mass a sensor including a sensor tube closed at a distal end, the sensor tube disposed within a lumen of an insertion tube, the insertion tube having an open distal end, the insertion tube provided with a first aperture adjacent the open end thereof, the sensor tube provided with a second aperture adjacent the closed end thereof, said sensor capable of measuring at least interstitial fluid pressure;
   (b) aligning the first and second apertures of the insertion and sensor tubes, respectively, so that at least part of the sensor tube is in interstitial fluid communication with the tissue mass;
   (c) measuring interstitial fluid pressure at a point in a path through the tissue mass while at least part of the sensor tube is in interstitial fluid communication with the tissue mass;
   (d) measuring interstitial fluid pressure at another point in said path through the tissue mass while at least part of the sensor tube is in interstitial fluid communication with the tissue mass;
   (e) repeating steps (c) through (d), wherein a first increase in interstitial fluid pressure is an indication of a pathologic condition in the tissue mass;
   (f) removing said sensor tube from said insertion tube and inserting a tissue marker into the insertion tube so that it extends from the open distal end of the insertion tube into the tissue mass at a point within said tissue mass where said pathologic condition is located.

2. The method of claim 1, further comprising the step of removing said insertion tube from said tissue mass and leaving said tissue marker in said tissue mass at the point where said pathologic condition is located.

3. The method of claim 1, wherein the step of inserting a tissue marker comprises inserting a hookwire.

4. The method of claim 1, wherein said pathologic condition is a tumor.

5. A method for marking the location of a tumor within a tissue mass, comprising the steps of:

inserting into the tissue mass a sensor including a sensor tube closed at a distal end, said sensor tube disposed within a lumen of an insertion tube having an open distal end, said insertion tube provided with a first aperture adjacent the open end thereof, said sensor tube provided with a second aperture adjacent the closed end thereof, said sensor capable of measuring at least interstitial fluid pressure;

(b) aligning the first and second apertures of the insertion and sensor tubes, respectively, so that at least part of the sensor tube is in communication with the tissue mass;

(c) measuring at least interstitial fluid pressure at a point in the tissue mass while at least part of the sensor tube is in communication with the tissue mass, wherein a first increase in at least interstitial fluid pressure is an indication that the insertion and sensor tubes have entered a tumor in the tissue mass;

(d) removing said sensor tube from said insertion tube and inserting a tissue marker into the insertion tube so that it extends from the open distal end of the insertion tube into the tissue mass at a point within said tissue mass where the tumor is located; and (e) removing said insertion tube from said tissue mass and leaving said tissue marker in said tissue mass at the point where the tumor is located.

* * * * *

UNITED STATES PATENT AND TRADEMARK OFFICE
CERTIFICATE OF CORRECTION

PATENT NO. : 5,396,897
DATED : March 14, 1995
INVENTOR(S) : Rakesh K. Jain, et. al.

It is certified that error appears in the above-indentified patent and that said Letters Patent is hereby corrected as shown below:

In the Abstract, line 11, delete "prodding", and insert therefor-- providing--.
In the Abstract, line 23, delete "prodded"; and insert therefor -- provided --.
Column 10, line 35, delete "tube-provided"; and insert therefor-- tube porvided --.

Signed and Sealed this

Ninth Day of May, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,396,897
DATED : March 14, 1995
INVENTOR(S) : Rakesh K. Jain et al.

It is certified that error appears in the above-indentified patent and that said Letters Patent is hereby corrected as shown below:

Column 1, lines 8-9: please delete "supposed" and insert therefor -- supported --;

Column 1, line 26: please delete "imposer" and insert therefor -- important --;

Column 1, line 34: please delete "witch" and insert therefor -- within --;

Column 2, line 35: please delete "micropiper" and insert therefor -- micropipet --;

Column 2, line 44: please delete "micropiper" and insert therefor -- micropipet --;

<u>In the Abstract of the Disclosure:</u>

In the penultimate line, please delete "deuce" and insert therefor -- device --.

Signed and Sealed this

Twenty-first Day of May, 1996

*Attest:*

BRUCE LEHMAN

*Attesting Officer*   *Commissioner of Patents and Trademarks*